(12) United States Patent
Thomas

(10) Patent No.: US 8,408,061 B2
(45) Date of Patent: *Apr. 2, 2013

(54) SEQUENTIALLY FIRED HIGH DYNAMIC RANGE NDT/NDI INSPECTION DEVICE

(75) Inventor: Andrew Thomas, Westford, MA (US)

(73) Assignee: Olympus NDT, Waltham, MA (US)

( * ) Notice: Subject to any disclaimer, the term of this patent is extended or adjusted under 35 U.S.C. 154(b) by 431 days.

This patent is subject to a terminal disclaimer.

(21) Appl. No.: 12/629,565

(22) Filed: Dec. 2, 2009

(65) Prior Publication Data

US 2011/0126624 A1    Jun. 2, 2011

(51) Int. Cl.
*G01N 29/04* (2006.01)

(52) U.S. Cl. .......................................... 73/602

(58) Field of Classification Search ................... 73/602, 73/620, 625, 628; 600/443, 447; 341/155
See application file for complete search history.

(56) References Cited

U.S. PATENT DOCUMENTS

| 4,530,243 | A | * | 7/1985 | Lund et al. | 73/633 |
| 5,373,741 | A | * | 12/1994 | Volkmann et al. | 73/602 |
| 6,063,033 | A | * | 5/2000 | Haider et al. | 600/447 |
| 7,506,546 | B2 | * | 3/2009 | Cuffe et al. | 73/602 |
| 7,757,557 | B2 | * | 7/2010 | Thomas et al. | 73/602 |
| 7,924,189 | B2 | * | 4/2011 | Sayers | 341/139 |
| 7,963,166 | B2 | * | 6/2011 | Thomas | 73/631 |
| 8,001,842 | B2 | * | 8/2011 | Thomas | 73/602 |
| 2011/0132092 | A1 | * | 6/2011 | Thomas | 73/627 |

* cited by examiner

*Primary Examiner* — J M Saint Surin
(74) *Attorney, Agent, or Firm* — Ostrolenk Faber LLP

(57) ABSTRACT

An apparatus for performing ultrasonic inspection of an object, during one measurement on the object, triggers a sequence of excitations of the probe system and receives a sequence of substantially identical echo signals reflected from the object, and further scales each echo signal to different degrees to increase and extend the dynamic range of the echo signals. An A/D converter is then used to digitize the scaled signal sequentially in a manner which dispenses the need for using numerous A/D converters and the associated filters. The digitized signal samples are then combined to produce a single digital output in a manner that is not overflowed and with desirable resolution.

20 Claims, 5 Drawing Sheets

SEQUENTIALLY FIRED HIGH DYNAMIC RANGE NDT/NDI INSPECTION DEVICE

FIELD OF THE INVENTION

The present invention relates to non-destructive testing and inspection devices (NDT/NDI) and more particularly, to a high dynamic range analog to digital conversion system and method which utilizes a sequence of pulse-receive acquisition cycles to realize a single high dynamic range measurement.

BACKGROUND OF THE INVENTION

The testing and examination of complex structures, without damaging them, is now of great importance in a wide range of industrial situations. The use of NDT/NDI ultrasound (UT), phased-array (PA), and eddy current (EC) measurement modalities are perhaps the most ubiquitous such methodology. UT methods are now used to measure the geometric properties (such as thickness) of test objects, and detect and characterize static defects or anomalies in metal, non-metal, or fiber composite structures in real time. EC methods are now used to detect and characterize static defects or anomalies in metal structures in real time. A large range of techniques for both UT and EC methods, from simple manual scanning to computer-controlled multi-axis tomography systems, are in use or under development.

Although the embodiments of the present disclosure may be used for UT, EC and other measurement modalities, the following background pertains only to UT.

Two primary groups of existing NDT/NDI ultrasonic (UT) systems are now described. The first group being exemplified by such products as the instant assignee's Epoch 4 Plus product. Competitive products available from General Electric are known as the USM 35X, USN 58L and USN 60 NDT/NDI UT systems. In general, this group of UT systems utilizes highly complex analog front ends that contain many parts which pose especially difficult problems in terms of calibration, reliability, set up time, consistency of results and optimization for specific usages and settings.

Typically this group of UT systems includes a probe system which is placed against the object to be tested and works in conjunction with numerous analog circuits such as gain calibrators, preamplifiers and attenuators, variable gain amplifiers, and high pass and low pass analog filters that operate over many different frequency bands and which need to be carefully calibrated and maintained.

As a result, this group of UT systems presents limitations and drawbacks to designers and users of such equipment, which impact their troubleshooting and repair owing to their complexity. More specifically, the limitations include such issues as matching input impedances seen by the probe system which changes with different gain amplifiers that are switched in and out of the signal path. This adversely impacts the frequency response and introduces various gain nonlinearities. It poses issues of calibration, as analog circuits are switched in and out of the signal path.

To overcome problem noted above, a second group of UT systems emerged represented by Olympus NDT Epoch XT and associated patent applications, such as US 2007/0084288. Representative technology of this group of flaw detectors involve splitting an input analog signal while converting it to digital form, into larger and/or smaller signal channels; scaling the input signal on the larger and/or smaller signal channels such that the smaller signal channels have higher resolution than the larger signal channels; sampling the larger and smaller signal channels using separate A/D converters; and selecting the output signals with the highest resolution that are not saturated. Due to the expansion or shrinkage of range of signal during the signal processing, flaw detectors using this group of technique are called 'High Dynamic Range (HDR)' flaw detectors.

These existing HDR digitizer designs employ two or more analog to digital converters synchronized to sample in unison. Typically the analog to digital converter outputs immediately enter a logic process that combine them into a single high dynamic range digital output signal that is typically sent to a digital memory device for storage. For identification purposes, these currently existing HDR designs are referred to as 'Parallel HDR' designs.

The use of Parallel HDR designs provides many advantages such as providing UT inspection with more accurate and more easily readable and consistent inspection results with a shorter and simpler process of calibration and adjustment prior to use. The use of Parallel HDR also enables many other capabilities such as adjusting the respective sample times to compensate for all sources of timing skew, preventing saturation of the input stage of each channel's preamplifier to prevent signal distortion from affecting the inputs to the other channels, adjusting the frequency response of each channel to substantially match, as well as adjusting the overall frequency response of the apparatus, detecting a channel overflow condition in one or more of the channels having higher gain and merging the multiple channels into a continuous output stream, etc.

However, Parallel HDR digitizer designs present the drawbacks associated with using two or more analog to digital converters. Such drawbacks include elevated hardware cost and the need for more circuit board space which is undesirable for a highly miniaturized product.

SUMMARY OF THE INVENTION

The invention disclosed herein avoids or ameliorates the aforementioned drawbacks and problems related to existing ultrasonic inspection devices, including complicated analog circuitry, high manufacturing cost, lower inspection measurement performance, and circuit board space.

It should be noted that although the embodiments of the present disclosure are described in relation to ultrasonic inspection devices and methods it is not limited in this regard. Indeed, the embodiments may also be applied to acoustic and eddy current (EC) inspection instruments, including, but not limited to, phased array and eddy current array (ECA) technologies. Furthermore, although the embodiments of the present disclosure are described in relation to the use of single element, dual element, or two independent probes for inspection, many other probe system types and connection topologies may be used.

Accordingly, it is a general object of the present disclosure to provide an ultrasonic inspection device with a high degree of circuit miniaturization, high and versatile performance, and low manufacturing cost.

It is a further object of the present disclosure to provide an ultrasonic inspection device using a high dynamic range digitizer solution that employs a minimum number of analog to digital converters and supporting circuitry while achieving high and versatile performance typically provided by Parallel HDR products.

It is a further object of the present disclosure to provide an ultrasonic inspection device that, within one measurement process cycle, employs sequential pulser excitations of a probe system multiple times, scales and digitizes the respective response signal for each excitation for high dynamic range, and subsequently provides inspection results by selecting or recomposing the response signals.

It is a further object of the present disclosure to provide a means for detecting a channel overflow condition in one or more of the channels having higher signal sensitivity; and a means for merging the multiple channels into a steady output stream.

It is yet a further object of the present disclosure to provide a means to represent the HDR measurement data in logarithmic or linear amplitude scale as a data output or a display image.

An embodiment which realizes the foregoing objectives may comprise an inspection device configured for inspecting a test object and including an acoustical probe system and an acoustical transmitter. A digital logic device, configured to trigger the transmitter to cause a sequence of excitations of the probe system to produce a sequence of consecutive acoustical waves upon a location of the test object, is operable with the probe system, which probe system, or other probe system, is further configured to receive a sequence of reflected acoustical waves and to produce a sequence of corresponding electrical signals. A receiver has a plurality of signal processing channels, each channel being configured to scale the echo signals to a different degree and to produce a sequence of corresponding scaled signals. A multiplexer is configured to select the scaled signals from the processing channels during successive acquisition cycles corresponding to the aforementioned excitations, and an analog to digital converter coupled to the multiplexer is configured to digitize the selected scaled signals and to produce a sequence of digitized signal samples. These samples are stored in a partitioned digital memory. The digital logic device is so configured as to process the digitized signal samples to produce a composite signal output which is optimized for a dynamic range of the analog to digital converter.

Other features and advantages of the present invention will become apparent from the following description of the invention that refers to the accompanying drawings.

DETAILED DESCRIPTION OF THE PREFERRED EMBODIMENT OF THE PRESENT INVENTION

Figure 1:
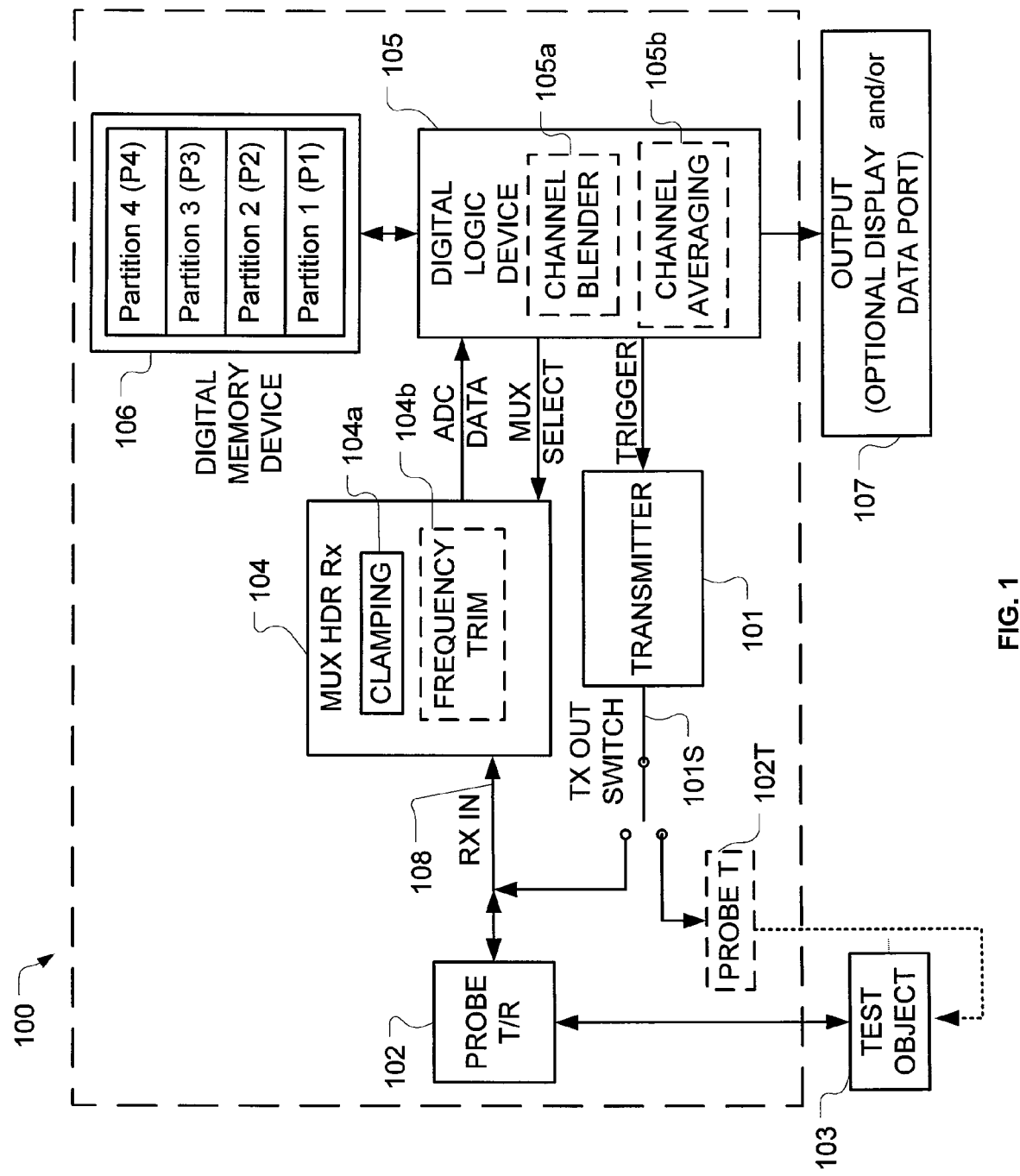
FIG. 1 is a schematic view of the preferred embodiment of the Sequentially Fired High Dynamic Range Inspection Device according to present invention.

Referring to FIG. 1, the preferred embodiment of a Sequentially Fired High Dynamic Range Inspection Device 100 comprises a transmitter 101 driving a probe system 102, or 102T and a multiplexed high dynamic range receiver (MUX HDR Rx) 104 coupled to receive signals from the probe system 102. As can be well understood by those skilled in the art, device 100 may be optionally configured to operate in the 'pulse-echo' or 'thru-transmission' mode. Device 100 is in 'pulse-echo' mode when probe system 102 is connected to receiver 104 and transmitter 101 by TX OUT switch 1015. Device 100 is in 'thru-transmission' mode when probe system 102 is connected only to receiver 104 and probe 102T is connected only to transmitter 101 by TX OUT switch 1015. When in 'thru-transmission' mode, probe system 102 receives response signals resulting from the acoustic energy imparted by probe 102T on the opposite side of test object 103. A digital logic device (DLD) 105, a Digital Memory Device 106, and an output unit 107 that optionally includes a display and/or a data port interconnected as shown, interface and operate with the aforementioned devices as described more fully below. Device 100 is designed so that it can be used as a NDT/NDI inspection system with high dynamic range measurement sensitivity.

The embodiments described below are described in relation to the 'pulse-echo' measurement mode. Those skilled in the art will be able to readily apply these embodiments to the 'thru-transmission' measurement mode; therefore, an exemplary 'thru-transmission' measurement process is not described herein.

An exemplary 'pulse-echo' measurement process cycle is comprised of separate and successive signal acquisition cycles conducted in the manner described below. During one measurement process cycle using device 100, transmitter 101 is fired to excite probe system 102 in sequential fashion when it is placed on or scanned across a test object 103. Digital Logic Device (DLD) 105 controls the excitation of transmitter 101 by means of a transmitter trigger according to a predetermined sequence and number of excitations, as well as the time interval between each excitation. Response signals resulting from each signal acquisition cycle are received and digitized by receiver 104, then stored in Digital Memory Device 106 as sample data sets. Each sample data set is comprised of a series of contiguous discrete samples acquired during a signal acquisition cycle for a particular channel within receiver 104. A signal acquisition cycle typically occurs during the time interval between each excitation; however, the duration and the placement of the time interval may be adjusted as required—e.g. for a special measurement application.

The sample data set for a particular channel within MUX HDR Rx 104 is stored in a respective partition within Digital Memory Device 106 (i.e. P1, P2, P3 or P4). At the end of a measurement process cycle, each channel partition of Device 106 will contain a set of contiguous discrete samples that are indexed with respect to the start of each channel's signal acquisition cycle. Discrete samples from different channels (205a through d of FIG. 2) sharing the same 'sample index point' are considered to represent the same relative moment in time within the signal acquisition cycle. Because of the high degree of ultrasonic measurement repeatability for each signal acquisition cycle, the magnitude of each of these discrete samples is considered to be substantially the same as that of signals acquired from a high dynamic range acquisition system using separate dedicated ADCs for each scaled acquisition channel—i.e. 'a single fired parallel high dynamic range measurement system' (Parallel HDR), such as the one disclosed in the present applicant's co-pending U.S. patent application with U.S. Ser. No. 11/489,889.

Accordingly, the indexing method described above ensures that the successive sample sets acquired and stored for individual channels can be properly aligned when signal reconstruction takes place.

After all signal acquisition cycles that comprise a measurement process cycle are complete, DLD 105 will process the resulting aggregate of indexed sample data, preferably one 'discrete indexed sample set' at a time, continuing until all discrete indexed sample sets within a complete measurement cycle are processed. A 'discrete indexed sample set' is comprised of one discrete sample from each acquisition channel for a particular 'sample index point'.

Continuing with FIG. 1, DLD 105 selects from Digital Memory Device 106 for each sample index point the sample data associated with the channel with the highest resolution that is not saturated, and provides it to output 107. In the event that all samples in a discrete indexed sample set are saturated (overflowed), data indicative of a saturated signal will be provided to output 107. Sample data sent to output 107 may be provided in the form of a linear or logarithmic amplitude signal. Output 107 is preferably a display and/or a signal port.

Figure 2:
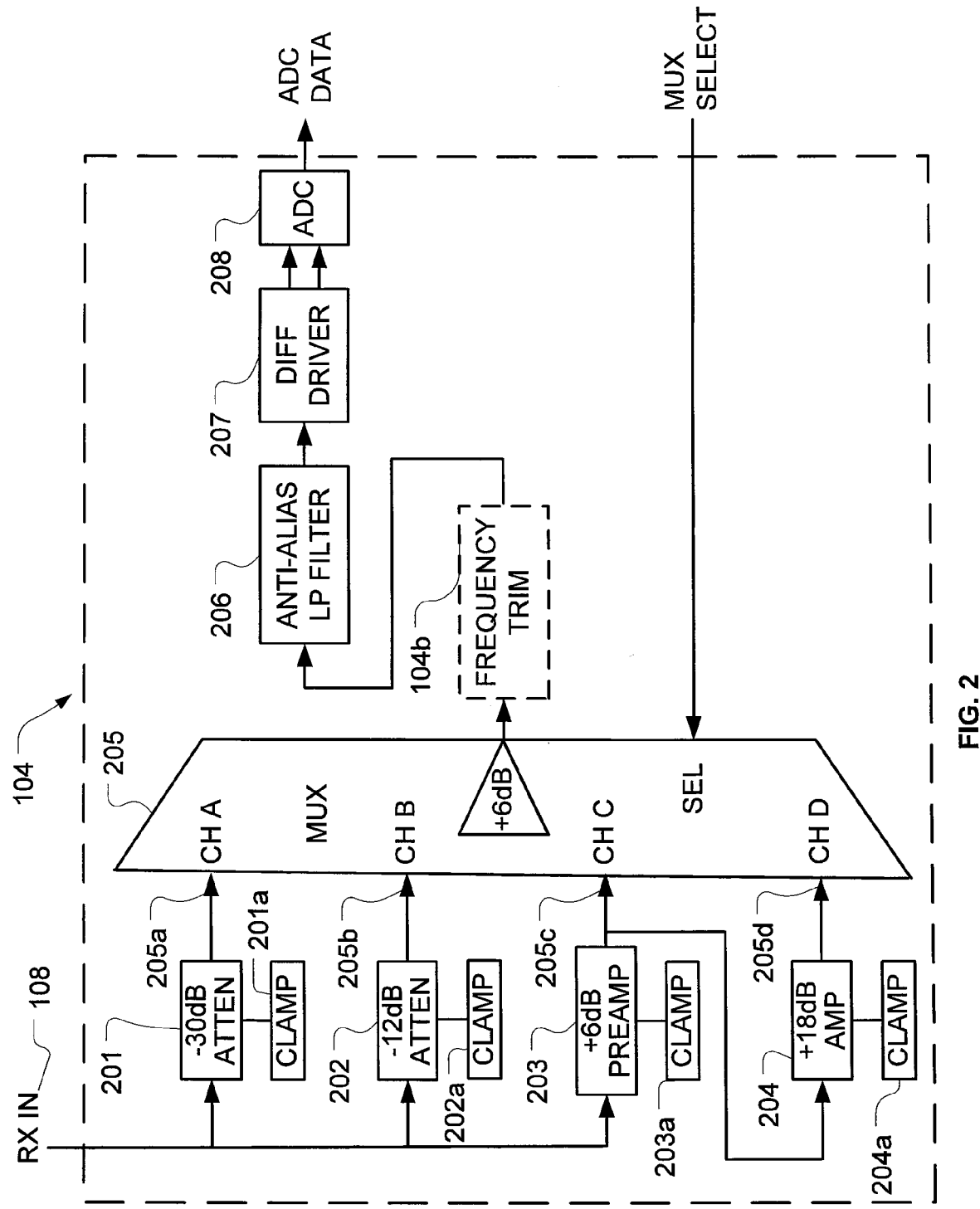
FIG. 2 is a schematic view of the Multiplexed High Dynamic Range Receiver of the preferred embodiment according to present invention.

Turning now to FIG. 2, the design of multiplexed high dynamic range receiver (MUX HDR Rx) 104 helps realize the presently disclosed Non-Destructive Test/Inspection (NDT/NDI) instrument, by employing multiple gain channels including attenuating amplifiers 201 and 202, and Gain amplifiers 203 and 204, with preferably increasing signal sensitivity respectively. High attenuation Attenuating amplifier 201, low attenuation Attenuating amplifier 202, low gain amplifier 203, and high gain amplifier 204 are associated with channels CH A, CH B, CH C, and CH D, respectively.

Referring back to FIG. 1 Digital Logic Device 105 sends a transmitter trigger to fire ultrasonic transmitter 101. In response to each trigger, transmitter 101 excites probe system 102, thereby inducing probe system 102 to transmit an ultrasonic signal into a test object 103. The ultrasonic signal reflects off of the defects encountered in the sound path and the far side of test object 103. These reflected echoes are received by probe system 102, converted into an electrical signal as the RX IN input to MUX HDR Rx 104. Digital Logic Device 105 stores the digitized signal samples of each selected channel into Digital Memory Device 106 as they are produced by MUX HDR Rx 104. The Digital Logic Device 105 stores each digitized signal resulting from selecting channel D 205d, channel C 205c, channel B 205b and channel A 205a sequentially into memory partitions P1, P2, P3 and P4 respectively.

Referring now to FIG. 2, the received RX IN signal is then attenuated or amplified by different amounts by Attenuating amplifiers 201 and 202, and Gain amplifiers 203 and 204. It should be noted that the combination of Attenuating amplifiers and Gain amplifiers should be construed in an exemplary manner. Digital Logic Device 105 sequentially selects a channel to be digitized by setting the MUX SELECT control. MUX 205 preferably passes the signal of the selected channel through an internal amplifier that amplifies the signal by a predetermined value, such as +6 dB. The MUX output is preferably bandwidth limited utilizing a Low Pass (LP) Anti-alias Analog Filter 206 and preferably converted from a single ended signal to a differential signal utilizing a differential driver 207 and converted by an Analog to Digital Converter (ADC) 208 into a digitized signal samples (ADC DATA). The signal acquisition cycle for the selected channel is complete after sufficient time has passed for the measurement event of interest, typically an echo response signal, to be received, digitized and stored.

It should be noted that it is within the scope of the present disclosure that the Analog to Digital Converter 208 may consist of two (or perhaps more) distinct ADCs, which operate on a time division multiplex basis to share the burden of converting the analog signals arriving from the four channels A, B, C and D. For example, while a first of the ADCs 208 processes the data from channel A, the second (not shown) would process the analog signals from channel B, and while the first of the ADCs processes the data from channel C (after a short delay), the second ADC would process the signals from channel D.

Figure 3:
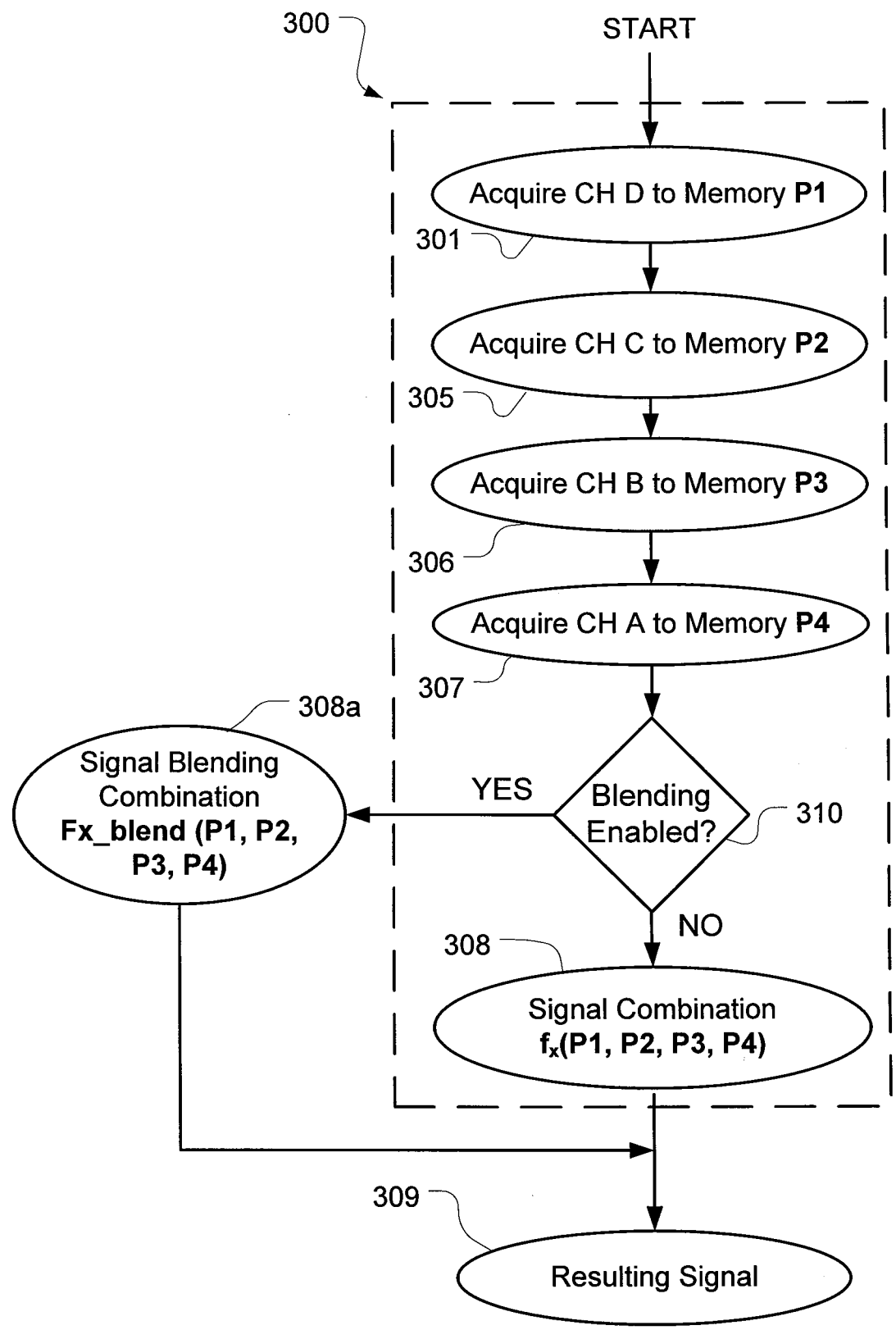
FIG. 3 is a flow chart illustrating the Digital Logic Device Measurement Process according to the preferred embodiment of present invention resulting in a High Dynamic Range Signal.

Referring to FIG. 3, measurement process 300 is controlled by DLD 105. A complete Measurement Process 300 is comprised of sequentially fired Acquisition Cycles (301, 305, 306, and 307), followed by a Signal Combination Function 308, and Resulting Signal 309 that may be rendered optionally as linear or logarithmic amplitude data. It should be noted that Blending Enable function 310 is set to 'NO' for the exemplary embodiment of the present invention to disable Channel Blender 105A of FIG. 1. Consequently, CH A acquisition cycle 307 is followed directly by Signal Combination Function 308 instead of Blended Signal Combination Function 308A. An alternate embodiment associated with Blending Enable function 310 being set to 'YES' is described later in the present disclosure.

It should be noted that one measurement process 300 is performed for one measurement location when probe system 102 is placed substantially still against test object 103.

Measurement Process 300 preferably begins with CH D acquisition cycle 301. CH D acquisition cycle 301 selects the CH D 205d input of Multiplexer 205, triggers Transmitter 101, and stores the resultant CH D digitized signal sample in Digital Memory Device 106 partition 1 (P1).

Next, CH C acquisition cycle 305 selects the CH C 203 input of Multiplexer 205c, triggers ultrasonic Transmitter 101, and stores the resultant CH C digitized signal sample in Digital Memory Device 106 partition 2 (P2).

Next, CH B signal acquisition cycle 306 selects CH B 205b input of Multiplexer 205, triggers ultrasonic Transmitter 101, and stores the resultant CH B digitized signal sample in Digital Memory Device 106 partition 3 (P3).

Next, CH A signal acquisition cycle 307 selects CH A 205a input of Multiplexer 205, triggers ultrasonic Transmitter 101, and stores the resultant CH A digitized signal sample in Digital Memory Device 106 partition 4 (P4). If any CH A signal sample point is saturated in acquisition process 307, the corresponding signal sample point is marked as saturated. However, unlike the process for the other channels, this time the saturated data will be used by the Signal combination function 308 and subsequently produce Resulting Signal 309.

Finally, when Blending Enable function 310 is set to 'NO', Signal combination function 308 reads all the digitized signal samples from their corresponding memory partitions and combines them to create the high dynamic range Resulting Signal 309.

The system of the present disclosure is capable of a dynamic range measurement sensitivity ranging from the maximum signal input that does not saturate ADC 208 when using the largest attenuating amplifier (CH A 205a) to the resolution, or noise limit, of the channel with the largest signal gain (CH D 205d). The dynamic range can easily exceed 100 dB with an upper frequency bandwidth limit of more than 25 MHz.

It should be noted that an indication of a saturation (overflow) condition detected by Digital Logic Device 105 for one or more of channels A, B, C or D may be stored within the respective memory partition(s) of Digital Memory Device 106 or within Digital Logic Device 105. The indication may be used for the purpose of selecting or reconstructing the output data provided to output 107 as described above.

System gain is set by Digital Logic Device 105 during the reading of Digital Memory Device 106. There is no need to adjust the system gain with an analog circuit. Digital Logic Device 105 can also produce the signal output according to other predetermined criterion in order to present output data for visual and/or analyzing purposes.

Referring again back to FIGS. 1 and 2, to ensure optimal signal fidelity with low distortion, clamping device 104a implemented in MUX HDR Rx 104 for attenuating amplifiers 201 and 202, and gain amplifiers 203 and 204. Clamping voltage thresholds for attenuating amplifiers 201 and 202 and gain amplifier 203 are set to levels such that the resulting output slightly exceeds the valid input range of ADC 208 when either channel A, B or C are selected. The clamp circuits 201a, 202a, 203a and 204a also limit the input voltage to the gain channel amplifiers to prevent them from entering into saturation.

The prevention of amplifier saturation is important because once in saturation, it takes a considerable amount of time for these components to return to their linear region of operation. By preventing the amplifiers from becoming saturated, the length of time the A/D converter is in the overflow condition is minimized, thereby allowing the higher resolution output data to be used sooner. The clamp circuit in gain amplifier 203 also serves to maintain a constant input impedance for input signal RX IN 108, regardless of the input signal level, up to a signal level or higher than the maximum input to channel A, i.e., attenuating amplifier 201. The input signal would become distorted if a constant input impedance is not maintained.

The present applicant recognizes that gain amplifier 204 does not require clamp 204a to maintain a constant input impedance for probe system 102 over its signal amplitude operating range because Gain amplifier 204 is isolated from probe system 102 by means of Gain amplifier 203. Therefore, an alternative amplifier circuit configuration can be used for gain amplifier 203 if it is needed to provide other benefits such as lower power or less circuit complexity.

The output of Multiplexer 205 is connected to Frequency Response Trim and Filter circuit 104b. A frequency response adjustment control signal (not shown) is used to make the frequency response of channels A, B, C and D match as closely as possible. This makes sure that all signal frequencies of interest have as close to the same gain as possible.

The detailed methods associated with the aforementioned Clamping device 104a and Frequency trim device 104b are disclosed in the present applicant's co-pending US patent application entitled ULTRASONIC FAULT DETECTION SYSTEM USING A HIGH DYNAMIC RANGE ANALOG TO DIGITAL CONVERSION SYSTEM (U.S. Ser. No. 11/489,889). The entire content of application Ser. No. 11/489,889 is herein incorporated by reference. The circuits disclosed and illustrated therein in FIG. 7, as elements 116, 118 and 120, and those drawing figures and the corresponding text are incorporated by reference as well. In addition to this, the circuits disclosed and illustrated therein in FIG. 8a in application Ser. No. 11/489,889, as elements 111a, 111b and 113, and those drawing figures and the corresponding text are incorporated by reference.

Detailed Description of the 'Selective Channel Averaging' (Secondary) Embodiment of the Present Invention The 'selective channel averaging' embodiment enhances the performance of the preferred embodiment by reducing acquired signal noise while maintaining optimal real-time performance.

Figure 4:
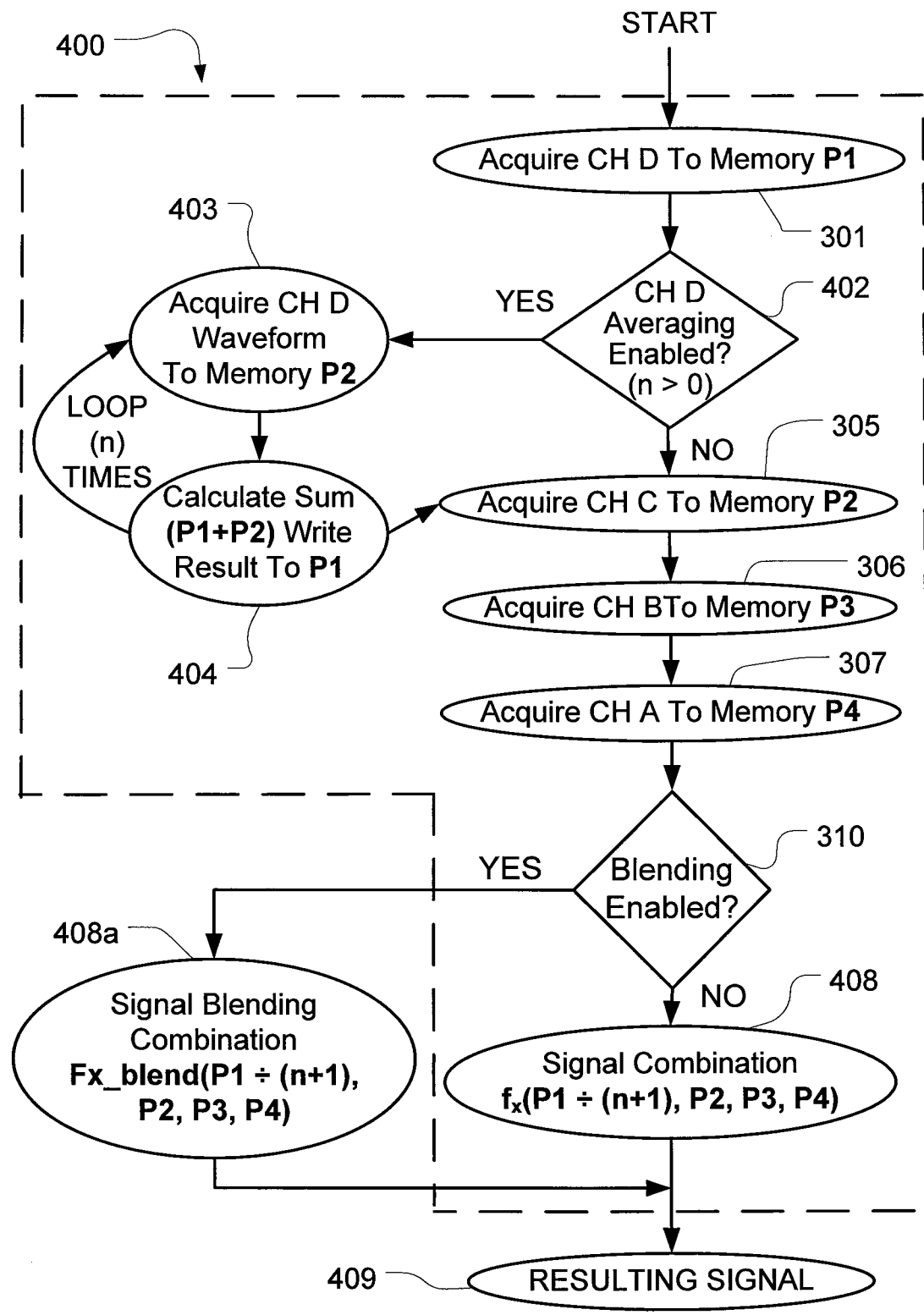
FIG. 4 is a flow chart illustrating the Digital Logic Device Measurement Process according to the Selective Channel Averaging embodiment of the present invention resulting in a High Dynamic Range Signal.

Referring now to FIG. 4, measurement process 400 is controlled by DLD 105. The Blending Enable function 410 is disabled for this secondary embodiment causing the output of process step 407 to be provided directly to process step 408. The alternate embodiment associated with the enabling of Blending Enable function 410 will be described later in the present disclosure.

Continuing with FIG. 4, it should be noted that elements 301, 305, 306, 307 and 310 of FIG. 4 perform the same function as the same numbered elements in FIG. 3. Along with overall measurement process 400, the elements unique to the secondary embodiment are CH D Averaging Enable 402, CH D acquisition cycle 403, Calculate Sum 404, Signal Combination 408, and Blended Signal Combination 408a.

In reference to FIG. 1 for both the preferred and secondary embodiment, when all channel acquisitions are completed that comprise a measurement process cycle, DLD 105 selects from Digital Memory Device 106 for each sample index point the sample data associated with the channel with the highest resolution that is not saturated (overflowed), and provides it to output 107. In the event that all samples in a discrete indexed sample set are saturated, data indicative of a saturated signal will be provided to output 107. Sample data sent to output 107 may be provided in the form of a linear or logarithmic amplitude signal. Output 107 is preferably a display and/or a signal port. Furthermore, an overflow indication of a saturation condition detected by Digital Logic Device 105 for one or more of channels A, B, C or D may be stored within the respective memory partition(s) of Digital Memory Device 106 or within Digital Logic Device 105.

Although for this embodiment Measurement Process 400 is applied only to the channel with the highest signal gain (CH D 205d), it may be applied to more than one channel if required.

It should be noted that one measurement process 300 or 400 is performed for one measurement location when probe system 102 is placed substantially still against test object 103.

Measurement Process 400 preferably begins with the CH D acquisition cycle 401. The CH D acquisition cycle 301 selects CH D 205d input on Multiplexer 205, triggers the Transmitter 101, and stores the resultant CH D digitized signal sample in Digital Memory Device 106 partition 1 (P1).

If CH D Averaging 402 is enabled (i.e. n>0), then CH D acquisition cycle 403 is next. CH D acquisition cycle 403 selects CH D 205d input on Multiplexer 205, triggers the Transmitter 101, and stores the resultant CH D digitized signal sample in Digital Memory Device 106 partition 2 (P2). Partition 2 (P2) is utilized as temporary storage (also known as a 'scratchpad') for the averaging processes 403 and 404.

Calculate Sum 404 then reads the stored CH D signals in partitions P1 and P2, then adds the signals together and writes the result (sum) signal back into P1. The scratchpad partition P2 is then available for re-use.

Digital Logic process 403 and 404 are executed for each averaging cycle required. For example, if Digital Logic processes 403 and 404 are executed seven (7) times, CH D will be averaged by a factor of eight (8). If any CH D signal sample point is saturated in acquisition processes 301 or 403, the corresponding signal sum sample point is marked as saturated in the Calculate Sum process 404. Marking the sum sample point as saturated prevents any saturated data from CH D from being used by the Signal combination function 408.

When the averaging process ends, or averaging is not enabled (i.e., n=0, CH C acquisition process 305 selects CH C 205c input on Multiplexer 205, triggers the ultrasonic Transmitter 101, and stores the resultant CH C digitized signal sample in Digital Memory Device 106 partition 2 (P2).

Next, CH B acquisition cycle 306 selects CH B 205*b* input on Multiplexer 205, triggers the ultrasonic Transmitter 101, and stores the resultant CH B digitized signal sample in Digital Memory Device 106 partition 3 (P3).

Next, CH A acquisition cycle 307 selects CH A 205*a* input on Multiplexer 205, triggers the ultrasonic Transmitter 101, and stores the resultant CH A digitized signal sample in Digital Memory Device 106 partition 4 (P4). If any CH A signal sample point is saturated in acquisition process 307, the corresponding signal sample point is marked as saturated. However, unlike the process for the other channels, this time the saturated data will be used by the Signal combination function 408 and subsequently produce Resulting Signal 409.

Finally, when Blending Enable function 310 is set to 'NO', Signal combination 408 reads all the digitized signal samples from their corresponding memory partitions and digitally combines them to create Resulting Signal 409. If CH D Averaging 402 is enabled (i.e. n>0), the Signal Combination process 408 completes the averaging process by dividing the final CH D sum of discrete signal sample amplitudes stored in partition 1 (P1) by the amount of averaging required (i.e., n+1).

The Selective Channel Averaging embodiment of the present disclosure has a dynamic range measurement sensitivity ranging from the maximum signal input that does not saturate ADC 208 when using the largest Attenuating amplifier (CH A 205*a*) to the resolution, or noise limit, of the channel with the largest signal gain (CH D 205*d*). The dynamic range can easily exceed 100 dB with an upper frequency bandwidth limit of more than 25 MHz.

System gain is set by the Digital Logic Device 105 during the reading of the Digital Memory Device 106. There is no need to adjust the system gain with an analog circuit. Digital Logic Device 105 can also produce the signal output according to other predetermined criterion in order to present output data for visual and analyzing purposes. Furthermore, the output data may be provided in a linear or logarithmic scale.

Detailed Description of Alternative Embodiments

The following design variations from the preferred embodiment should be recognized by those skilled in the art to be within the scope of the present disclosure. The detailed description of the following alternative embodiments focuses on the portion of the embodiments varied from the preferred embodiment, and should be construed to complement the preferred embodiment.

Alternative Embodiments Pertaining to Both the Preferred and Secondary Embodiments One variation is that Digital Logic Device 105 can be alternatively designed to so that the sequence of the acquisition cycles for CH A, CH B, CH C and CH D to be in any order deemed fit.

Another variation is to use a different number of channels and corresponding gain channels other than four for situations as deemed fit.

Further alternatively, using only one adjustable amplifier capable of producing a range of gains is also possible.

Yet another alternative design involves modifying the aforementioned Signal combination function 308. As described above, signal samples are retrieved by digital memory device 106 by DLD 105 after the acquisition cycles for all channels are complete. As an alternative to this approach, the digital signals may be combined as they are acquired in partial steps between acquisitions before all the acquisitions are complete for all channels.

For an alternative embodiment that pertains to the blending of channel acquisition data, reference is made once again to FIGS. 1, 3 and 4. The blending function is applied to discrete sample pairs from adjacent sensitivity channels that share a common sample index point (described earlier). More specifically, the blending function combines the adjacent partitions in digital memory device 106 in a manner which blends and/or adjusts portion of each digital output being used to avoid the saturated (overflowed) portion of the digital outputs and to minimize phase and/or amplitude discontinuity of the composite digital signal.

When Blending Enable function 310 is set to 'YES', Channel Blender 105A is enabled causing the immediate next step after CH A acquisition cycle 307 to be Signal Blending Combination 308A for the preferred embodiment, and Signal Blending Combination 408A for the secondary embodiment.

The detailed methods associated with the aforementioned channel blending are disclosed in the present applicant's co-pending US patent application entitled SAMPLE ERROR MINIMIZATION FOR HIGH DYNAMIC RANGE DIGITIZATION SYSTEMS (U.S. Ser. No. 12/605,769). The entire content of the application Ser. No. 12/605,769 is herein incorporated by reference. It should be noted that elements 504, 506, 508, and 510 of FIG. 5 in the present disclosure correspond to FIGS. 1, 2, 3 and 4 respectively in application Ser. No. 12/605,769. The circuits disclosed and illustrated in FIGS. 1, 2, 3 and 4 in application Ser. No. 12/605,769 and the corresponding text are incorporated by reference.

Figure 5:
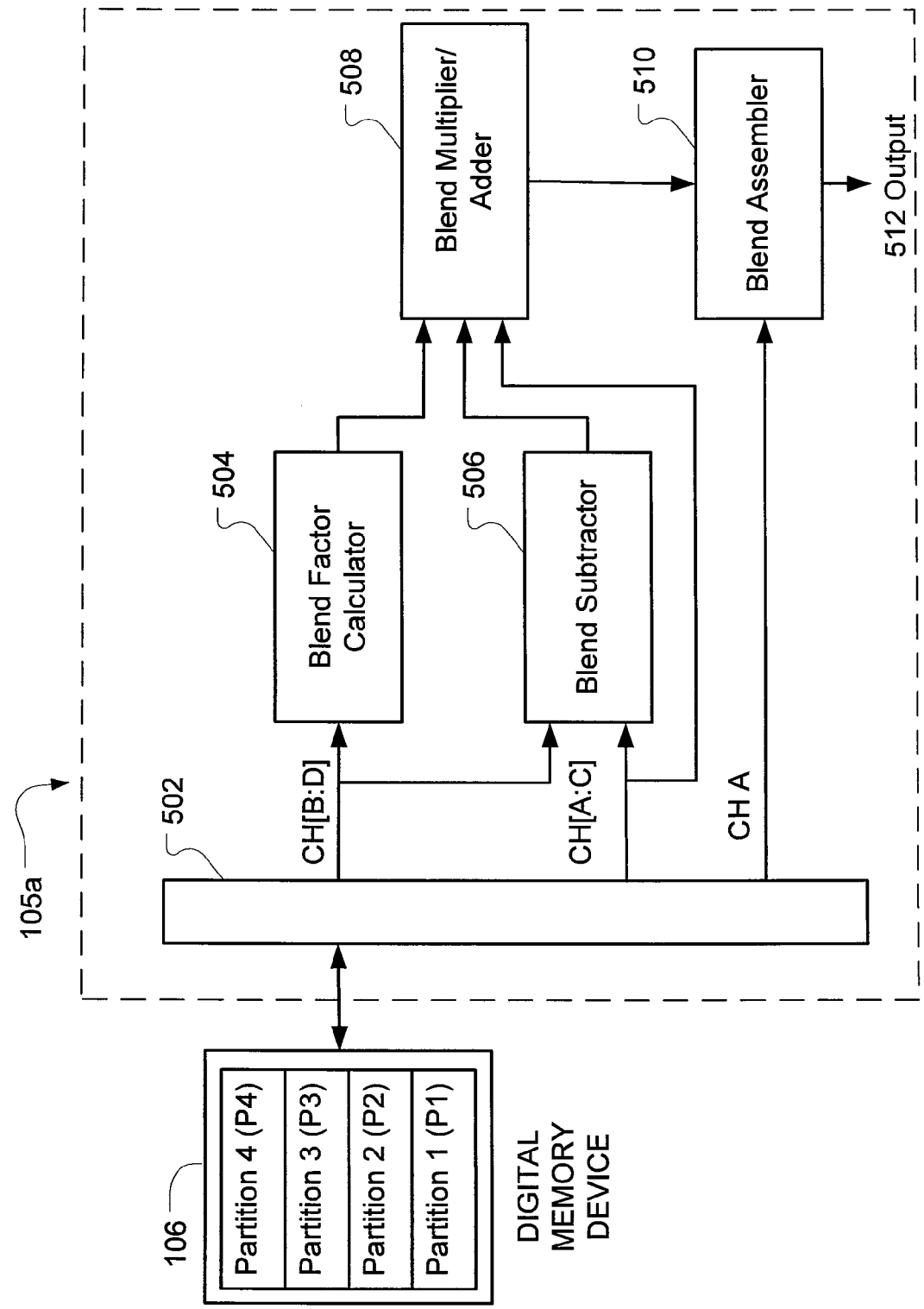
FIG. 5 is a block diagram of a blending circuit associated with Channel Blender 105a of FIG. 1.

The usage of the blending process is effective for both presently disclosed sequentially fired HDR design and parallel HDR design. Thus, as illustrated in FIG. 5 herein (as more fully disclosed in the aforementioned Ser. No. 12/605,769 patent application), an input circuit 502 represents the input into the blending circuit of the digital output signals from channels A, B, C and D stored in Digital Memory Device 106, some of which may indicate an overflow condition. The input circuit 502 feeds its output signals as shown in FIG. 5 to blend factor calculator 504, blend subtractor 506, blend multiplier/adder 508, and blend assembler 510. Output from blend factor calculator 504, blend subtractor 506, and input circuit 502 is provided to blend multiplier/adder 508, which, in turn, feeds its output to blend assembler 510, which also receives an input from input circuit 502 before producing the final output 512.

It should be noted that the sequential excitation and other teachings of the present disclosure may be applied to a system employing more than one analog to digital converter, such as the type disclosed in present applicant's co-pending U.S. patent application with U.S. Ser. No. 11/489,889.

Alternative Embodiments Pertaining Only to the Secondary Embodiment

Referring back to FIG. 4, Digital Memory Device 106 can be alternatively designed using a high bandwidth Digital Memory Device or Devices that would allow for faster processing of averaging processes 403 and 404. High Bandwidth memory would allow a design to utilize the increased memory bandwidth to compute the mathematical addition in real time, thus combining Digital Logic process 403 and 404 into a single state. A High Bandwidth memory device would eliminate the need for a temporary storage partition (scratchpad) for the calculation of the averaging process sum.

Another variation is that Digital Logic Device can be alternatively designed with Selective Averaging capability for CH D and CH C. Although CH C averaging is not typically necessary due to the lower level of noise.

Another variation is that Digital Logic Device can be alternatively designed with Selective Averaging dynamically or manually adaptable to CH D and/or any other channel or channels.

Another variation is that Digital Logic Device can be alternatively designed with the mathematical division of the CH D signal sum in a separate state. This division state could be inserted anywhere in between states 404, 305, 306, 307, and 408.

Although the present invention has been described in relation to particular exemplary embodiments thereof, many other variations and modifications and other uses will become apparent to those skilled in the art. It is preferred, therefore, that the present invention not be limited by the specific disclosure. For example, the scope of the present disclosure may be applied to a variety of NDT/NDI systems employing single-element, multi-element, and array probes for ultrasonic (UT), eddy current (EC) or other NDT/NDI systems.

What is claimed is:

1. An inspection device configured for inspecting a test object, comprising:
    a probe system;
    a digital logic device, configured to trigger the probe system, during a measurement at a given location on the test object, to cause a sequence of excitations of the probe system to produce a corresponding sequence of consecutive waves upon the location of the test object during the measurement, wherein the probe system, is further configured to receive a sequence of corresponding wave responses and to produce a sequence of corresponding electric signals;
    a receiver having a plurality of signal processing channels, each channel configured to scale the electric signals to a different degree and to produce a sequence of corresponding scaled signals;
    a channel selection device configured to select the scaled signals from the processing channels during successive acquisition cycles corresponding to the sequence of excitations;
    at least one analog to digital converter configured to digitize the selected scaled signals and to produce therefrom a sequence of digitized signal samples corresponding to the sequence of the excitations;
    a digital memory for storing the digitized signal samples; and
    wherein the digital logic device is configured to process the digitized signal samples to produce a composite signal output with a dynamic range that is higher than that of said analog to digital converter.

2. The device of claim 1, wherein successive ones of the electric scaled signals at the location have a substantially same wave shapes.

3. The device of claim 1, wherein the scaled signals are in an instrument sensitivity range from a maximum signal input to a minimum signal input.

4. The device of claim 1, wherein each of the excitations of the probe system, receiving of the signals, producing of the scaled signals, and digitizing and storing of the digitized signal samples are carried out in corresponding acquisition cycle.

5. The device of claim 4, wherein the measurement includes at least two acquisition cycles.

6. The device of claim 1, wherein the receiver further includes an anti aliasing filter.

7. The device of claim 1, wherein the receiver further includes a differential driver.

8. The device of claim 1, including a display for displaying the composite signal output and/or other inspection results on a linear or logarithmic amplitude scale.

9. The device of claim 1, wherein the digital memory has digital memory partitions and each digitized signal sample is stored in a corresponding digital memory partition.

10. The device of claim 9, further including overflow indications outputted by the analog to digital converter, and a blending circuit coupled to the digitized signal samples and to their respective overflow indications and configured to produce therefrom the composite signal output which combines the digitized signal samples in a manner which blends and/or adjusts at least a portion of each digitized signal sample being used to minimize phase and/or amplitude discontinuities of the composite signal output.

11. The device of claim 10, wherein the blending circuit includes:
    a blend factor calculator configured to calculate a respective blend factor for adjacent ones of the partitions, responsive to the overflow indications and the digitized signal samples;
    a blending subtractor for producing signal differences corresponding to the adjacent partitions; and
    a blending multiplier and adding circuit responsive to the signal difference and to the blend factors to produce respective scaled blended signals for the adjacent partitions.

12. The device of claim 11, in which the blending circuit further includes a blending assembler circuit responsive to said overflow indications and to said scaled blended signals to produce said composite digital signal.

13. The device of claim 1, in which the composite signal output is provided in the form of a linear signal.

14. The device of claim 1, in which the composite signal output is provided as a logarithmic amplitude signal.

15. The device of claim 1, in which the composite signal output is provided at a dynamic range which exceeds 100 dB, with an upper frequency bandwidth limit of more than 25 MHz.

16. The device of claim 1, further including a clamping circuit interposed electrically between the probe system and the analog to digital converter, to optimize signal fidelity with low distortion.

17. The device of claim 1, further comprising a frequency trim circuit interposed between the multiplexer and the analog to digital converter, and configured to obtain a matched frequency response for the plurality of signal processing channels.

18. The device of claim 1, wherein the probe system comprises a first probe component which is configured to excite the test object and a second probe component, for receiving the wave response and for producing the sequence of corresponding electric signals.

19. The device of claim 1, wherein the probe system is an acoustical probe system.

20. The device of claim 1, wherein the probe system is of a type which produces eddy currents in the test object.

* * * * *